(12) United States Patent
Kim et al.

(10) Patent No.: US 8,260,030 B2
(45) Date of Patent: Sep. 4, 2012

(54) INSPECTION METHOD

(75) Inventors: Hee-Tae Kim, Yongin-si (KR); Bong-Ha Hwang, Seoul (KR); Seung-Jun Lee, Seoul (KR); Kwang-Ill Kho, Seoul (KR)

(73) Assignee: Koh Young Technology Inc., Seoul (KR)

(*) Notice: Subject to any disclaimer, the term of this patent is extended or adjusted under 35 U.S.C. 154(b) by 348 days.

(21) Appl. No.: 12/748,801

(22) Filed: Mar. 29, 2010

(65) Prior Publication Data

US 2010/0246931 A1    Sep. 30, 2010

(51) Int. Cl.
G06K 9/00    (2006.01)

(52) U.S. Cl. ........................................... 382/141

(58) Field of Classification Search .......... 382/141–151, 382/282, 275, 294; 348/86–95, 125–134; 702/35–59
See application file for complete search history.

(56) References Cited

U.S. PATENT DOCUMENTS
2007/0172111 A1*    7/2007    Ikeda ............................ 382/149

FOREIGN PATENT DOCUMENTS

| CN | 1746667 A | 3/2006 |
|---|---|---|
| CN | 1865950 A | 11/2006 |
| EP | 1 462 997 A2 | 9/2004 |
| JP | 2002-288633 A | 10/2002 |
| JP | 2003-208616 A | 7/2003 |
| JP | 2004-144557 A | 5/2004 |
| JP | 2006-099758 A | 4/2006 |
| JP | 2008-185514 A | 8/2008 |
| KR | 1020020017532 A | 3/2002 |
| KR | 1020060053967 A | 5/2006 |
| KR | 100612933 B1 | 8/2006 |

* cited by examiner

*Primary Examiner* — Tarifur Chowdhury
*Assistant Examiner* — Abdullahi Nur
(74) *Attorney, Agent, or Firm* — Kile Park Goekjian Reed & McManus PLLC

(57) ABSTRACT

In order to set an inspection area, a measurement target is disposed onto a stage, a reference data of the measurement target is summoned, and a measurement data of the measurement target is acquired. Then, at least one feature object is selected in the measurement data and the reference data of the measurement target, and at least one feature variable for the selected feature object is extracted from each of the reference data and the measurement data. Thereafter, a change amount of the measurement target is produced by using the feature variable and a quantified conversion formula, and the produced change amount is compensated for to set an inspection area. Thus, the distortion of the measurement target is compensated for to correctly set an inspection area.

16 Claims, 13 Drawing Sheets

INSPECTION METHOD

CROSS REFERENCE TO RELATED APPLICATION

This application claims priority from and the benefit of Korean Patent Applications No. 2009-27162, filed on Mar. 30, 2009, and No. 2010-24689, filed on Mar. 19, 2010, which are hereby incorporated by reference for all purposes as if fully set forth herein.

BACKGROUND OF THE INVENTION

1. Field of the Invention

Exemplary embodiments of the present invention relate to an inspection method. More particularly, exemplary embodiments of the present invention relate to an inspection method for a measurement target in a shape measurement apparatus.

2. Discussion of the Background

Generally, at least one printed circuit board (PCB) is employed in an electronic device, and various circuit elements such as a circuit pattern, a connection pad part, a driver chip electrically connected to the connection pad part, etc. are mounted on the printed circuit board.

A shape measurement apparatus is typically used to check whether the various circuit elements are formed or configured good or not on the printed circuit board.

In a conventional shape measurement apparatus, a predetermined inspection area is set to inspect whether circuit elements are formed good or not in the inspection area. In a conventional method of setting an inspection area, an area, in which circuit elements are theoretically located, is simply set as an inspection area.

When the inspection area is set at a correct location, a measurement of a desired circuit element is performed well. However, in a measurement target such as a printed circuit board, distortion such as warp, twist, etc. of a base board may be generated. Thus, in the conventional method of setting an inspection area, the inspection area is not correctly set at a desired location, and a location corresponding to an image acquired in a camera of a photographing section is a little different from a location where a circuit element actually exists.

Thus, an inspection area is required to set to compensate for the distortion of the measurement target.

SUMMARY OF THE INVENTION

Exemplary embodiments of the present invention provide an inspection method capable of setting an inspection area in which distortion of a measurement target is compensated for.

Exemplary embodiments of the present invention also provide an inspection method capable of setting an inspection area in which distortion of a measurement target is compensated for, and correctly setting an inspection area through setting and verifying a feature including a plurality of shape patterns when similar patterns are adjacent on a board.

Additional features of the invention will be set forth in the description which follows, and in part will be apparent from the description, or may be learned by practice of the invention.

An exemplary embodiment of the present invention discloses an inspection method. The method includes disposing a measurement target onto a stage, summoning a reference data of the measurement target, acquiring a measurement data of the measurement target, selecting at least one feature object in the measurement data and the reference data of the measurement target, extracting at least one feature variable for the selected feature object from each of the reference data and the measurement data, producing a change amount of the measurement target by using the feature variable and a quantified conversion formula, and compensating for the produced change amount to set an inspection area.

The measurement target may include a printed circuit board, the feature object may include at least one of a pattern, a hole, and a shape of a circuit element and a corner point formed on the printed circuit board, and the feature variable may include at least one of a coordinate of a point, a slope of a line, a size of a line and a difference between coordinates of two points.

For example, the change amount of the measurement target may include at least one of a change amount of vertical slope and a change amount of height. The change amount of the vertical slope may be acquired using a geometric transformation produced by comparing a plane shape of the feature object selected in the reference data with a plane shape of the feature object corresponding to the selected feature object in the acquired measurement data.

In an exemplary embodiment, before producing the change amount of the measurement target by using the feature variable and a quantified conversion formula, the method may further include setting the conversion formula by using at least one of a location change, a slope change, a size change and a transformation degree between the feature variable of the reference data and the feature variable of the measurement data. Setting the conversion formula may include setting a coordinate space corresponding to the feature object of the reference data to a first coordinate space, setting a coordinate space corresponding to the feature object of the measurement data to a second coordinate space, and expressing a coordinate conversion relation equation including at least one of the location change, the slope change, the size change and the transformation degree to convert the first coordinate space to the second coordinate space as a conversion equation including at least one unknown. Setting the inspection area may include expressing the feature variable of the reference data and the feature variable of the measurement data as the conversion equation, acquiring the unknown included in the conversion equation to finalize the conversion formula, and setting the inspection area in which distortion incurred from the change amount is compensated for by using the finalized conversion formula.

Another exemplary embodiment of the present invention discloses an inspection method. The method includes disposing a measurement target onto a stage, summoning a reference data including a first feature object of the measurement target, acquiring a measurement data of the measurement target, extracting a second feature object corresponding to the first feature object from the measurement data, comparing a plane shape of the first feature object with a plane shape of the second feature object to check and quantify a geometric transformation to produce a change amount in a vertical direction of the measurement target, and setting an inspection area based on the change amount.

For example, the first feature object may have a polygon shape.

An exemplary embodiment of the present invention discloses an inspection method. The inspection method includes setting a measurement area on a board, summoning a reference data for the measurement area, acquiring a measurement data for the measurement area, setting at least one feature block in the measurement area by a block, comparing a first shape information of the feature block in the reference data with a second shape information of the feature block in the measurement data to acquire a conversion relation between the reference data and the measurement data, and compensating for distortion by using the conversion relation to set an inspection area for inspecting a measurement target.

A plurality of shapes may be in the shape information corresponding to the feature block. At least two shapes of the shapes in the shape information may be substantially the same. The shape information may have a two-dimensional identifier. The feature block may be plural. In an exemplary embodiment, comparing the shape information, corresponding to the feature block in the reference data and the shape information corresponding to the feature block in the measurement data to acquire the conversion relation between the reference data and the measurement data may include selecting at least two feature blocks from the plurality of feature blocks, and acquiring a quantified conversion formula between the reference data and the measurement data by using the selected at least two feature blocks.

In an exemplary embodiment, setting at least one feature block for predetermined shape information in the measurement area by a block may include setting a comparison feature block to compare the shape information and setting a verification feature block to verify validity of the set inspection area of the measurement target. The method may further include judging whether the set inspection area of the measurement target is valid or not by using the verification feature block. Judging whether the set inspection area of the measurement target is valid may include converting the verification feature block by using the conversion relation, measuring the verification feature block, comparing the converted feature block and the measured verification feature block to judge whether location difference between the converted feature block and the measured verification feature block is within a tolerance, and resetting the conversion relation when the location difference is out of the tolerance.

In an exemplary embodiment, the method may further include overlaying the reference data and the measurement data. In addition, the method may further include further include removing a noise pattern in the feature block by using the overlay.

According to the above, the change amount of the measurement target incurred from the geometric distortion of the measurement target is considered to compensate for the change amount of the measurement target. Thus, an inspection area for the measurement target may be correctly set.

In addition, a predetermined shape information in the measurement area set on the board is set as the feature block by a block, and the shape information corresponding to the feature block of the reference data and the measurement data is compared to acquire the conversion relation between the reference data and the measurement data, thereby correctly setting the inspection area.

In addition, even though similar patterns are adjacent on the board, the feature block may be designated without confusion. Also, the inspection area may be correctly set through a step of setting and verifying the feature block including a plurality of shape patterns.

In addition, in case that the shape information corresponding to the feature block has a plurality of shapes, the conversion relation may be more correctly acquired. In case that at least two shapes in the shape information are substantially the same, the shape information is compared by one block to reduce mistakability.

In addition, when the shape information in the feature block has a two-dimensional identifier, mistakability may be reduced in comparing the shape information.

In addition, a work such as an inspection of parts may be performed based on the set inspection area, to thereby more correctly judge whether the board is good or bad.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
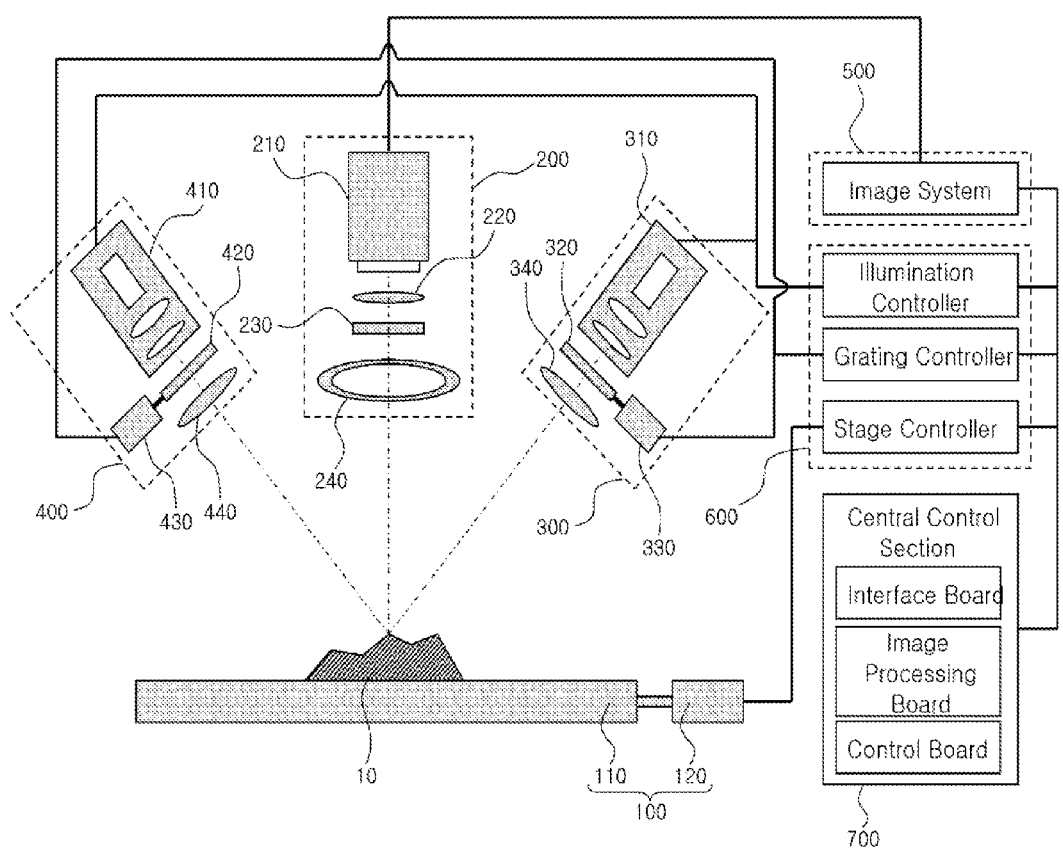
FIG. 1 is a schematic view illustrating a three-dimensional shape measurement apparatus using an inspection method according to an exemplary embodiment of the present invention.

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments of the invention are described herein with reference to cross-sectional illustrations that are schematic illustrations of idealized example embodiments (and intermediate structures) of the present invention. As such, variations from the shapes of the illustrations as a result, for example, of manufacturing techniques and/or tolerances, are to be expected. Thus, example embodiments of the present invention should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, an inspection method according to an exemplary embodiment of the present invention will be described with reference to the accompanying drawings.

FIG. 1 is a schematic view illustrating a three-dimensional shape measurement apparatus using an inspection method according to an exemplary embodiment of the present invention.

Referring to FIG. 1, a three-dimensional shape measurement apparatus using an inspection method according to an exemplary embodiment of the present invention may include a measurement stage section 100, an image photographing section 200, first and second is illumination sections 300 and 400, an image acquiring section 500, a module control section 600 and a central control section 700.

The measurement stage section 100 may include a stage 110 supporting a measurement target 10 and a stage transfer unit 120 transferring the stage 110. In an exemplary embodiment, according as the measurement target 10 moves with respect to the image photographing section 200 and the first and second illumination sections 300 and 400 by the stage 110, a measurement location may be changed in the measurement target 10.

The image photographing section 200 is disposed over the stage 110 to receive light reflected by the measurement target 10 and measure an image of the measurement target 10. That is, the image photographing section 200 receives the light that exits the first and second illumination sections 300 and 400 and is reflected by the measurement target 10, and photographs a plan image of the measurement target 10.

The image photographing section 200 may include a camera 210, an imaging lens 220, a filter 230 and a lamp 240. The camera 210 receives the light reflected by the measurement target 10 and photographs the plan image of the measurement target 10. The camera 210 may include, for example, one of a CCD camera and a CMOS camera. The imaging lens 220 is disposed under the camera 210 to image the light reflected by the measurement target 10 on the camera 210. The filter 230 is disposed under the imaging lens 220 to filter the light reflected by the measurement target 10 and provide the filtered light to the imaging lens 220. The filter 230 may include, for example, one of a frequency filter, a color filter and a light intensity control filter. The lamp 240 may be disposed under the filter 230 in a circular shape to provide the light to the measurement target 10, so as to photograph a particular image such as a two-dimensional shape of the measurement target 10.

The first illumination section 300 may be disposed, for example, at a right side of the image photographing section 200 to be inclined with respect to the stage 110 supporting the measurement target 10. The first illumination section 300 may include a first illumination unit 310, a first grating unit 320, a first grating transfer unit 330 and a first condensing lens 340. The first illumination unit 310 may include a light source and at least one lens to generate light, and the first grating unit 320 is disposed under the first illumination unit 310 to change the light generated by the first illumination unit 310 into a first grating pattern light having a grating pattern. The first grating transfer unit 330 is connected to the first grating unit 320 to transfer the first grating unit 320, and may include, for example, one of a piezoelectric transfer unit and a fine linear transfer unit. The first condensing lens 340 is disposed under the first grating unit 320 to condense the first grating pattern light exiting the first grating unit 320 on the measurement target 10.

For example, the second illumination section 400 may be disposed at a left side of the image photographing section 200 to be inclined with respect to the stage 110 supporting the measurement target 10. The second illumination section 400 may include a second illumination unit 410, a second grating unit 420, a second grating transfer unit 430 and a second condensing lens 440. The second illumination section 400 is substantially the same as the first illumination section 300 described above, and thus any further description will be omitted.

When the first grating transfer unit 330 sequentially moves the first grating unit 320 by N times and N first grating pattern lights are illuminated onto the measurement target 10 in the first illumination section 300, the image photographing section 200 may sequentially receive the N first grating pattern lights reflected by the measurement target 10 and photograph N first pattern images. In addition, when the second grating transfer unit 430 sequentially moves the second grating unit 420 by N times and N first grating pattern lights are illuminated onto the measurement target 10 in the second illumination section 400, the image photographing section 200 may sequentially receive the N second grating pattern lights reflected by the measurement target 10 and photograph N second pattern images. The 'N' is a natural number, and for example may be four.

In an exemplary embodiment, the first and second illumination sections 300 and 400 are described as an illumination apparatus generating the first and second grating pattern lights. Alternatively, the illumination section may be more than or equal to three. In other words, the grating pattern light may be illuminated onto the measurement target 10 in various directions, and various pattern images may be photographed. For example, when three illumination sections are disposed in an equilateral triangle form with the image photographing section 200 being the center of the equilateral triangle form, three grating pattern lights may be illuminated onto the measurement target 10 in different directions. For example, when four illumination sections are disposed in a square form with the image photographing section 200 being the center of the square form, four grating pattern lights may be illuminated onto the measurement target 10 in different directions.

The image acquiring section 500 is electrically connected to the camera 210 of the image photographing section 200 to acquire the pattern images from the camera 210 and store the acquired pattern images. For example, the image acquiring section 500 may include an image system that receives the N first pattern images and the N second pattern images photographed in the camera 210 and stores the images.

The module control section 600 is electrically connected to the measurement stage section 100, the image photographing section 200, the first illumination section 300 and the second illumination section 400, to control the measurement stage section 100, the image photographing section 200, the first illumination section 300 and the second illumination section 400. The module control section 600 may include, for example, an illumination controller, a grating controller and a stage controller. The illumination controller controls the first and second illumination units 310 and 410 to generate light, and the grating controller controls the first and second grating transfer units 330 and 430 to move the first and second grating units 320 and 420. The stage controller controls the stage transfer unit 120 to move the stage 110 in an up-and-down motion and a left-and-right motion.

The central control section 700 is electrically connected to the image acquiring section 500 and the module control section 600 to control the image acquiring section 500 and the module control section 600. Particularly, the central control section 700 receives the N first pattern images and the N second pattern images from the image system of the image acquiring section 500 to process the images, so that three-dimensional shape of the measurement target may be measured. In addition, the central control section 700 may control a illumination controller, a grating controller and a stage controller of the module control section 600. Thus, the central control section may include a image processing board, a control board and an interface board.

In order to measure a shape of a printed circuit board employed in the measurement target 10 by using the above-described three-dimensional shape measurement apparatus, first, an inspection area for measurement is set. When the inspection area is set, the three-dimensional shape measurement apparatus measures a portion in the inspection area based on the inspection area.

Hereinafter, an inspection method will be described in detail with the accompanying drawings.

Figure 2:
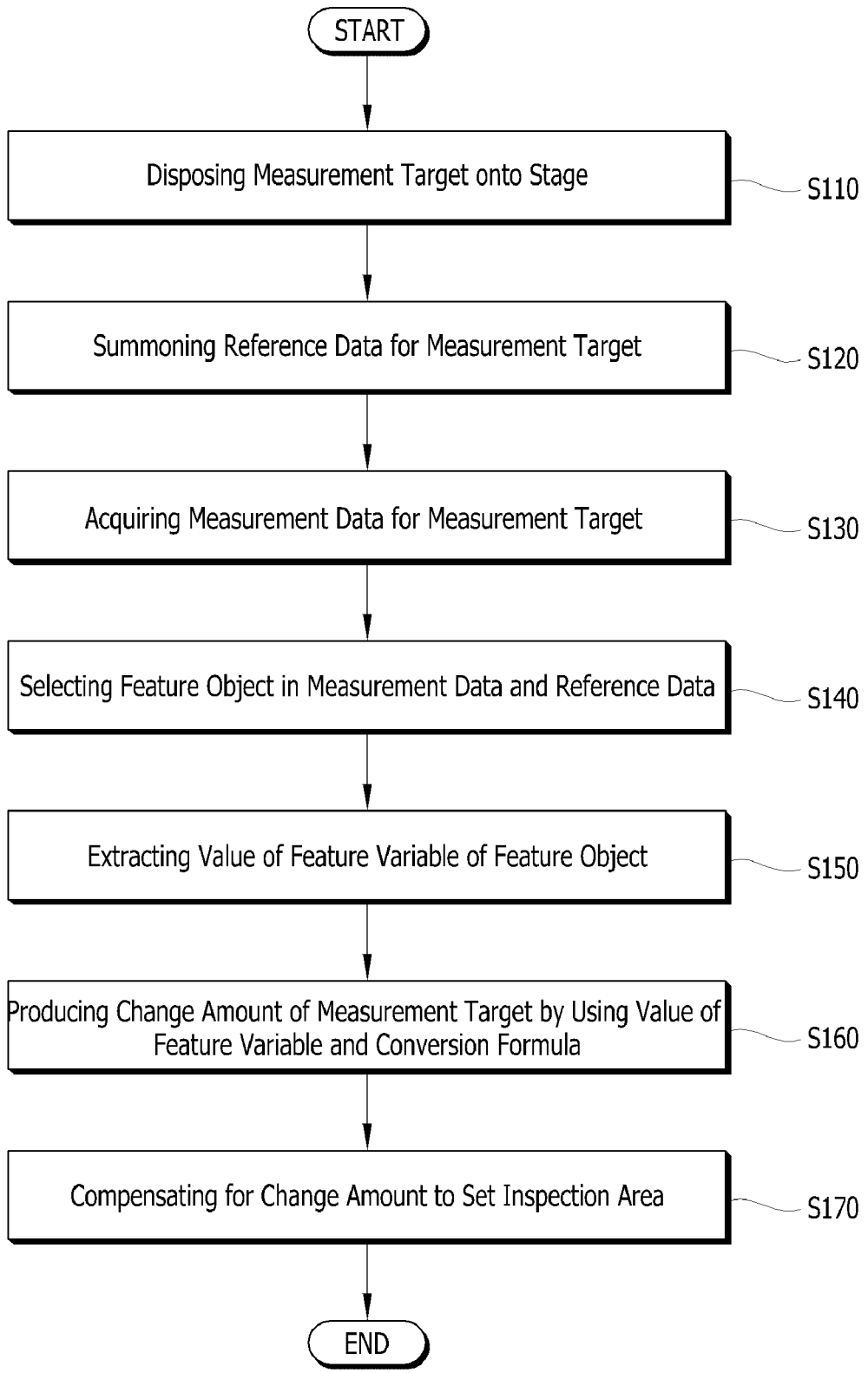
FIG. 2 is a flow chart illustrating an inspection method according to an exemplary embodiment of the present invention.

FIG. 2 is a flow chart illustrating an inspection method according to an exemplary embodiment of the present invention.

Referring to FIGS. 1 and 2, in order to set an inspection area according to an exemplary embodiment of the present invention, first, the measurement target 10 is disposed on the stage 110 in step S110.

The measurement target 10 may include, for example, a printed circuit board or a part, a pattern, etc. formed on a printed circuit board.

Then, a reference data for the measurement target 10 is summoned in step S120.

The reference data may include theoretical information corresponding to a design reference for the measurement target 10. The reference data may include a reference location, a reference shape, etc. of various circuit elements formed or disposed on the measurement target 10. That is, the reference data may include a location, a shape, etc. that the circuit elements disposed on the measurement target 10 theoretically owns.

In an exemplary embodiment, the reference data may be obtained from CAD information or gerber information in which a shape of the measurement target 10 is recorded. The CAD information or the gerber information may include design information of the measurement target 10.

In another exemplary embodiment, the reference data may be acquired from learning information that is obtained in a learning mode. The learning mode may include, for example, sequentially, searching board information in a database, learning a bare board in case that the board information is not in the database, and storing the board information in the database after the board information is produced by learning the bare board.

That is, in the learning mode, a bare board of a printed circuit board is learned and design reference information of the printed circuit board is acquired, and the reference data may be acquired by obtaining the learning information through the learning mode.

Thereafter, a measurement data for the measurement target is acquired in step S130.

The measurement data represents for the data obtained by measuring the measurement target 10, for example, the data for the photographed image of the measurement target 10. The photographed image may be two-dimensional image. The measurement data may include a formation location, a formation shape, etc. of various circuit elements actually formed or disposed on the measurement target 10. That is, the measurement data may include a location, a shape, etc. in which the circuit elements are actually formed on the measurement target 10.

Figure 3:
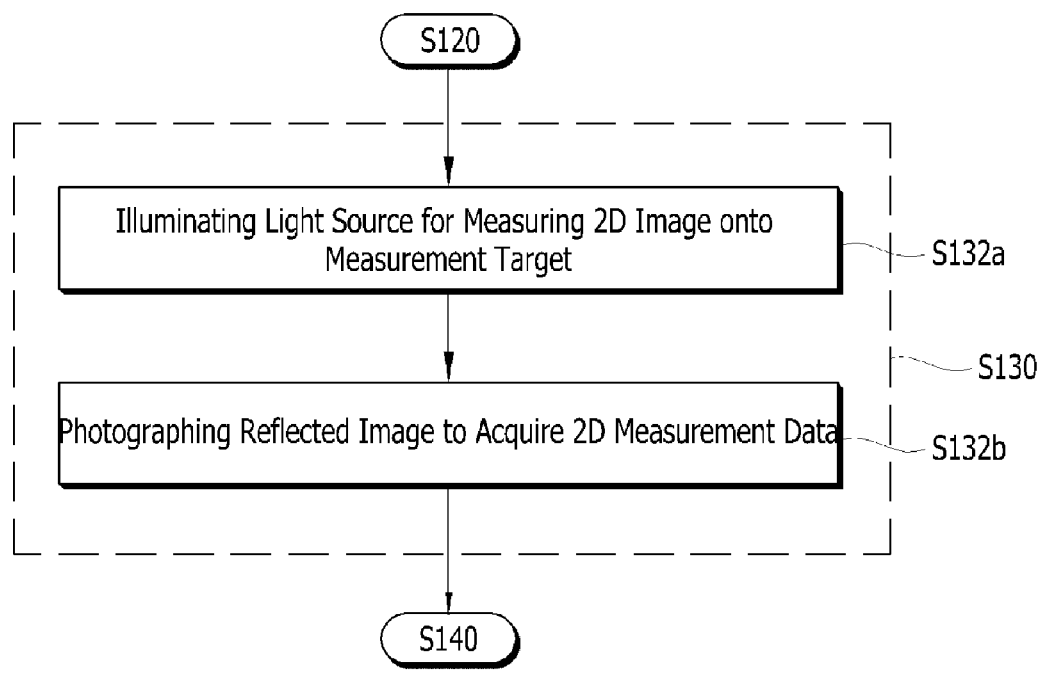
FIG. 3 is a flow chart illustrating an exemplary embodiment for a detail method of acquiring a measurement data for a measurement target in the inspection method illustrated in FIG. 2.

FIG. 3 is a flow chart illustrating an exemplary embodiment for a detail method of acquiring a measurement data for a measurement target in the inspection method illustrated in FIG. 2.

Referring to FIGS. 1 to 3, in order to acquire the measurement data for the measurement target 10, first, a light source for measuring a two-dimensional image is illuminated onto the measurement target in step S132a.

The light source for measuring the two-dimensional image may include, in an exemplary embodiment, a lamp 240 illustrated in FIG. 1. Alternatively, the three-dimensional shape measurement apparatus illustrated in FIG. 1 may include a two-dimensional image measurement light source for various purposes, which may be employed in the light source for measuring the two-dimensional image.

Then, the reflected image of the illuminated light is photographed to acquire a two-dimensional measurement data in step S132b.

Particularly, the light generated by the light source for measuring the two-dimensional image is illuminated onto the measurement target 10. When the illuminated light is reflected by the measurement target 10, the reflected image is photographed by the image photographing section 200 illustrated in FIG. 1 to acquire the two-dimensional measurement data.

Figure 4:
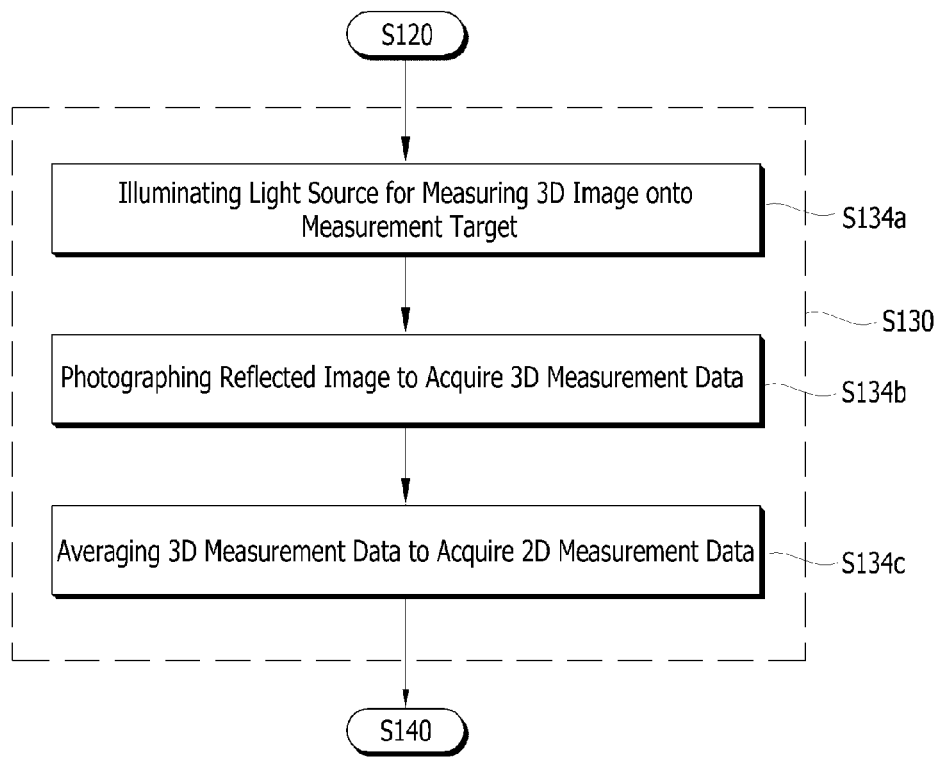
FIG. 4 is a flow chart illustrating another exemplary embodiment for a detail method of acquiring a measurement data for a measurement target in the inspection method illustrated in FIG. 2.

FIG. 4 is a flow chart illustrating another exemplary embodiment for a detail method of acquiring a measurement data for a measurement target in the inspection method illustrated in FIG. 2.

Referring to FIGS. 1, 2 and 4, in order to acquire the measurement data for the measurement target 10, first, a light source for measuring a height-based three-dimensional image is illuminated onto the measurement target in step S134a.

The light source for measuring a height-based three-dimensional image may include, in an exemplary embodiment, the first illumination section 300 and the second illumination section 400 illustrated in FIG. 1. Alternatively, the light source for measuring a height-based three-dimensional image may include more than or equal to three illumination sections as described in FIG. 1.

Then, the reflected image of the illuminated light is photographed to acquire a height-based three-dimensional measurement data in step S134b.

Particularly, the pattern light generated by the light source for measuring a height-based three-dimensional image is illuminated onto the measurement target 10. When the illuminated pattern light is reflected by the measurement target 10, the reflected image is photographed by the image photographing section 200 illustrated in FIG. 1 to acquire a pattern image. As described in FIG. 1, the pattern image acquired by the image photographing section 200 is stored in the image acquiring section 500, and the pattern image is processed in the central control section 700 to acquire a height-based three-dimensional measurement data.

Thereafter, the height-based three-dimensional measurement data is averaged to acquire a two-dimensional measurement data in step S134c.

Even though the measurement data based on three-dimensional height does not directly include the two-dimensional measurement data, the measurement data based on three-dimensional height may be averaged to easily acquire the two-dimensional measurement data.

For example, detail processes for acquiring two-dimensional measurement data by averaging the height-based three-dimensional measurement data are as follows.

$$i_n = a + b\cos(\phi + \Delta_n), \left(\text{where } \Delta_n = 0, \frac{\pi}{2}, \pi, \frac{3\pi}{2}\right)$$

$$i_1 = a + b\cos\phi$$

$$i_2 = a + b\cos(\phi + \pi/2)$$

$$i_3 = a + b\cos(\phi + \pi)$$

$$i_4 = a + b\cos(\phi + 3\pi/2)$$

$$i_1 = a + b\cos\phi$$

$$i_2 = a - b\sin\phi$$

$$i_3 = a - b\cos\phi$$

$$i_4 = a + b\sin\phi$$

$$\therefore a = \frac{i_1 + i_2 + i_3 + i_4}{4}$$

In the above, 'i' is light intensity acquired by the image photographing section 200 during acquiring the height-based three-dimensional measurement data, and 'a' and 'b' are a mean value and an amplitude, respectively. For example, when the height-based three-dimensional measurement data is acquired by using four grating pattern lights, 'a' is obtained as expressed above, which may be used as the two-dimensional measurement data.

Referring again to FIGS. 1 and 2, then, the measurement data for the measurement target 10 and the reference data for the measurement target 10 are compared to select at least one feature object in step S140.

Figure 5:
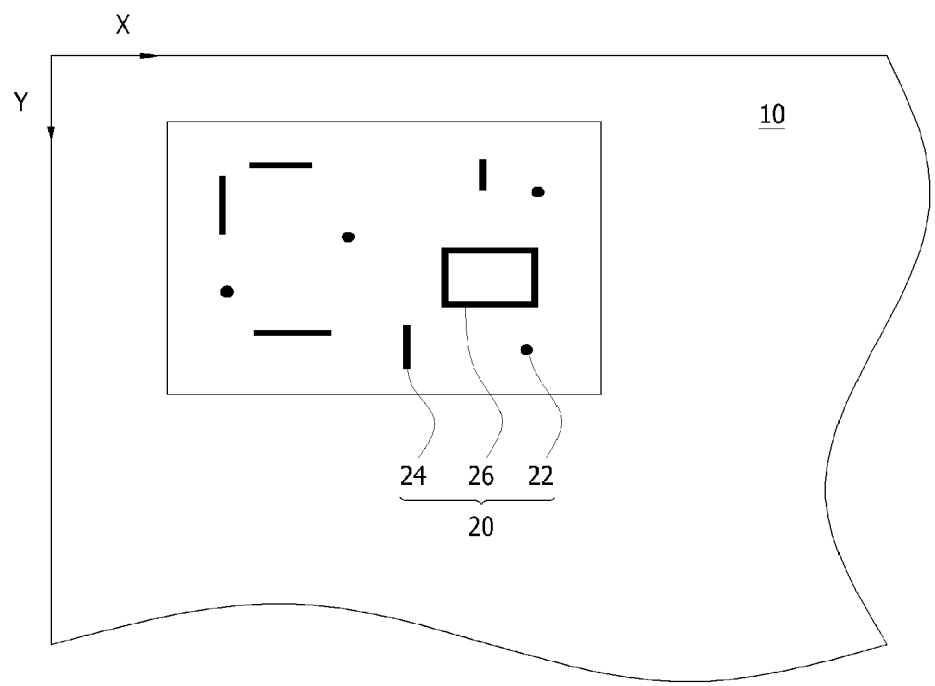
FIG. 5 is a plan view illustrating a feature object in the inspection method illustrated in FIG. 2.

FIG. 5 is a plan view illustrating a feature object in the inspection method illustrated in FIG. 2.

Referring to FIGS. 1, 2 and 5, a feature object 20 is a target in which a change amount between the measurement data and the reference data, which will be described later, is measured. The feature object 20 exists in the measurement target 10. In principle, the feature object 20 may be any object existing in the measurement target 10. For example, the feature object 20 may include at least one of a point 22, a line 24 and a figure including a point and a line such as a quadrangle 26. The line may include a straight line and curve line, and the figure may include a mathematically undefined figure in addition to mathematically defined figures such as a circle, a polygon, etc.

In selecting the feature object 20, an object, the change amount of which is easily measured and which is frequently found on the measurement target 10, may be selected as the feature object 20. For example, when the measurement target 10 is a printed circuit board, at least one of patterns, holes, which are formed on the printed circuit board, shapes of various circuit elements and corner points of the patterns may be selected as the feature object 20.

After comparing the measurement data for the measurement target 10 and the reference data for the measurement target 10, an object existing in both the measurement data and the reference data may be selected as the feature object 20.

Thereafter, value of at least one feature variable of the selected feature object 20 is extracted from the reference data and the measurement data in step S150.

For example, the feature variable may include at least one of a coordinate of a point, a slope of a line, a size of a line and a difference between coordinates of two points. When the feature object 20 is a point 22, the feature variable may be a coordinate of the point 22, a radius of the point 22, etc. When the feature object 20 is a line 24, the feature variable may be coordinates of both end points of the line 24, a coordinate of a center of the line 24, a slope of the line 24, a length of the line 24, a width of the line 24, etc. When the feature object 20 is a figure, for example, a quadrangle 26, the feature variable may be a coordinate of each point of the quadrangle 26, a slope of each side of the quadrangle 26, a length of each side of the quadrangle 26, a difference between coordinates of points of the quadrangle 26, etc.

Then, a change amount of the measurement target 10 is produced by using the value of the feature variable and a quantified conversion formula in step S160.

The conversion formula is a formula mathematically converting the reference data into the measurement data. For example, the conversion formula may include a coordinate conversion formula according to an affine conversion or a perspective conversion, in which point-to-point relation is expressed as a first-order form in an n-dimensional space.

The change amount of the measurement target 10 corresponds to a distortion degree of the measurement target 10, which is incurred from warp, twist, etc. The change amount of the measurement target 10 may be incurred from measurement geometric distortion generated in measuring the measurement target 10. For example, the change amount of the measurement target 10 may be generated by geometric distortion, which is generated by warp, twist, etc. of the measurement target 10.

FIGS. 6 to 12 are schematic views illustrating change amount of the measurement target according to geometric distortion of the measurement target.

Referring to FIGS. 6 to 12, the change amount of the measurement target 10 may include at least one of a change amount AV of vertical slope, a change amount H of height, a change amount AH of horizontal slope and a change amount (x1-x0, y1-y0) of a location (x,y).

Figure 6:
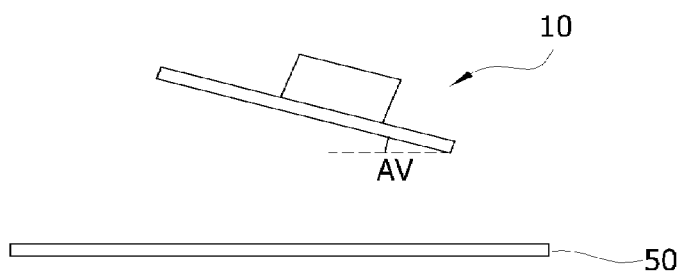
FIGS. 6 to 12 are schematic views illustrating a change amount of the measurement target according to geometric distortion of the measurement target.
Figure 7:
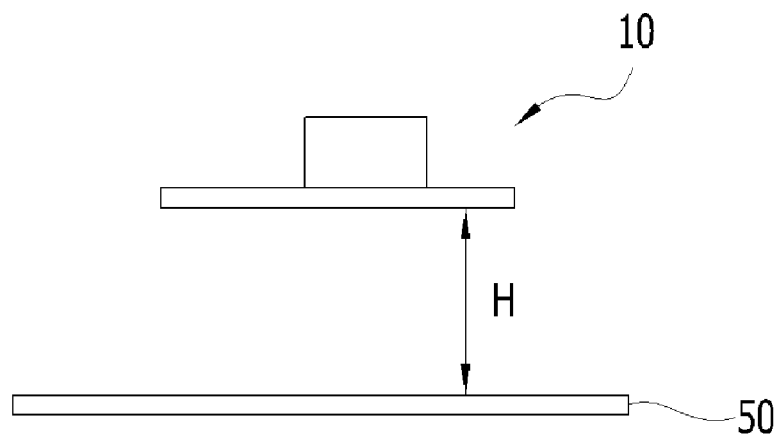
Figure 8:
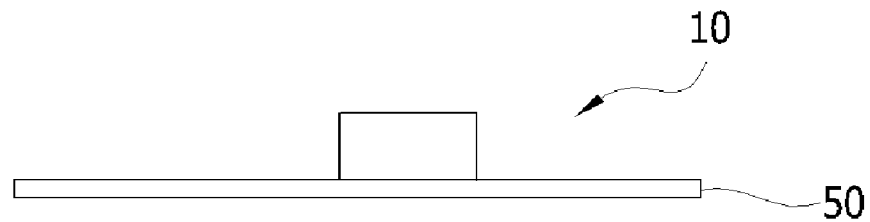
Figure 9:
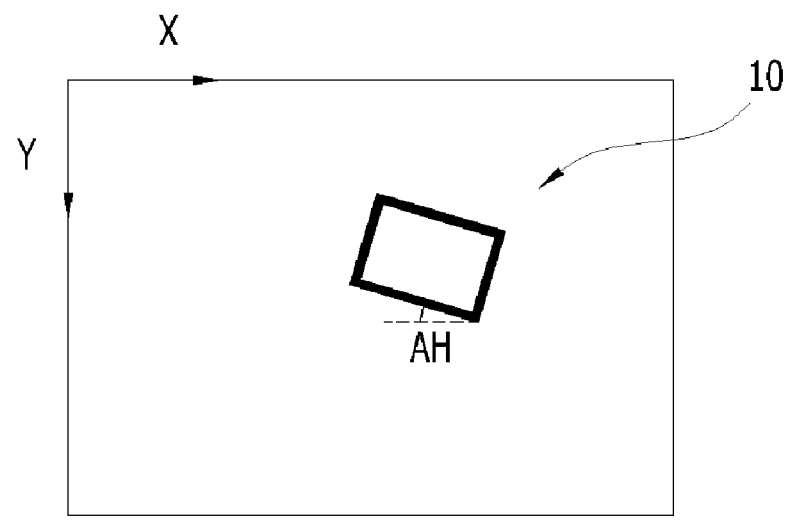
Figure 10:
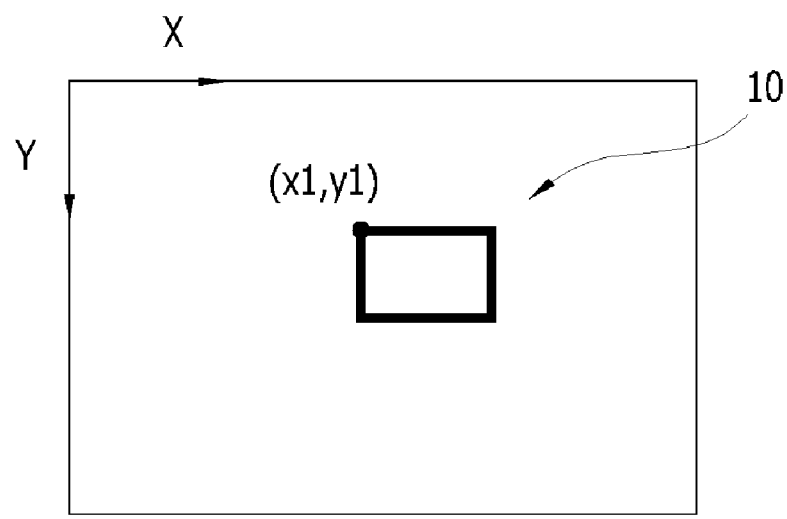
Figure 11:
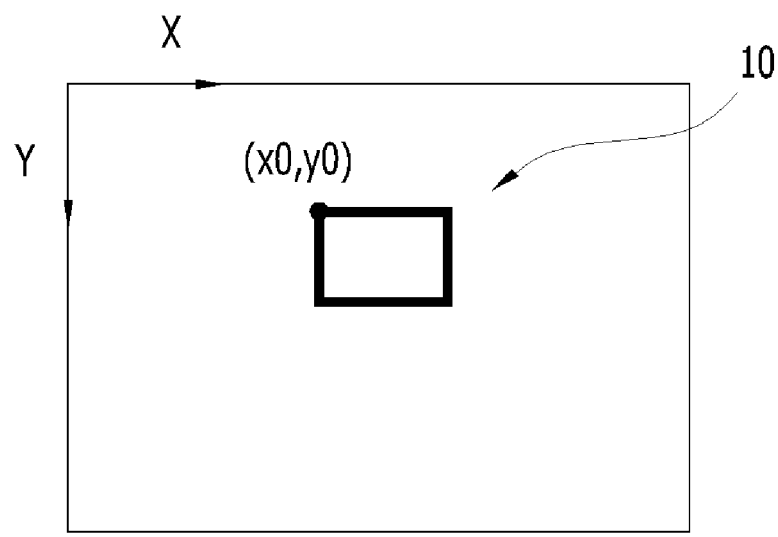
Figure 12:
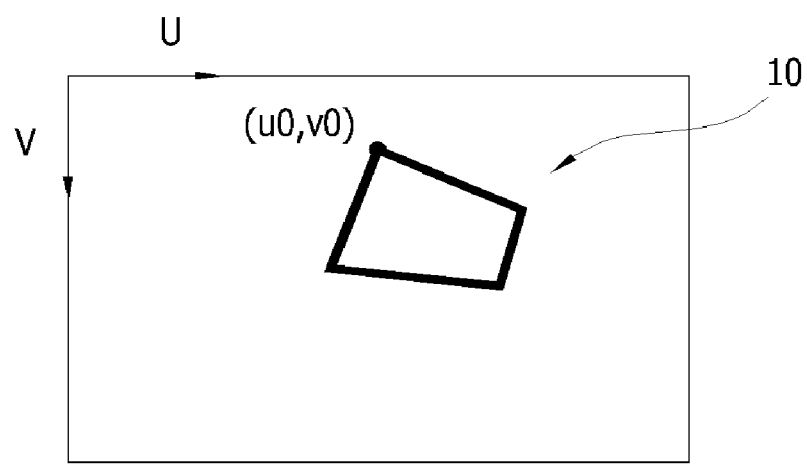

FIG. 6 is a side view showing a state that various geometric distortions exists in the measurement target 10. FIG. 7 is a side view showing a state that the change amount AV of vertical slope is removed from the various geometric distortions. FIG. 8 is a side view showing a state that the change amount H of height is removed from the geometric distortions in FIG. 7. Reference numeral 50 indicates an ideal plane, and corresponds to the reference data. FIG. 9 is a plan view of FIG. 8. FIG. 10 is a plan view showing a state that the change amount AH of horizontal slope is removed from the geometric distortions in FIG. 9. FIG. 11 is a plan view showing a state that the change amount (x1-x0, y1-y0) of the location (x,y) is removed from the geometric distortions in FIG. 10. FIG. 11 is a plan view showing a state that the change amount AV of vertical slope, the change amount H of height, the change amount AH of horizontal slope and the change amount (x1-x0, y1-y0) of the location (x,y) are removed from the various geometric distortions. FIG. 12 is a plan view in which the measurement target 10 shown in FIG. 6 is projected. Thus, FIG. 11 illustrates an example of the reference data, and FIG. 12 corresponding to FIG. 6 illustrates an example of the measurement data.

In FIG. 12, since a left portion is located nearer to the image photographing section 200 (refer to FIG. 1) than a right portion in the measurement target 10, a measurement image corresponding to a measurement data of the left portion is photographed large. In addition, since both the left portion and the right portion are located nearer to the image photographing section 200 than the ideal plane 50, a measurement image corresponding to a measurement data is photographed larger than the real size.

In other words, in case that the left portion, as described above, is photographed larger than the right portion in the image photographing section 200 by the geometric distortion of the measurement target 10, so that the measurement target 10 is measured in a shape similar to a trapezoid, the height-based three-dimensional reference data for the measurement target 10, which is described above, and the measured three-dimensional measurement data for the measurement target 10 are compared to check and compensate for the geometric transformation of the measurement target 10 according to a perspective conversion, i.e., the transformation corresponding to the change amount of vertical slope of the measurement target 10.

In an exemplary embodiment, the conversion formula may be determined by using at least one of a location change, a slope change, a size change and a transformation degree between value of the feature variable of the reference data and value of the feature variable of the measurement data. That is, as described above, a location change, a slope change, a size change, a transformation degree, etc. are generated in the reference data described as an example in FIG. 11 and the measurement data described as an example in FIG. 12. The transformation degree corresponds to a change generated by distance transformation or projection transformation.

The changes may be set as the conversion formula in advance. That is, a coordinate space corresponding to the feature object of the reference data in FIG. 11 is set to a first coordinate space, for example, (X,Y) space, and a coordinate space corresponding to the feature object of the measurement data in FIG. 12 is set to a second coordinate space, for example, (U,V) space. Then, a coordinate conversion relation equation for at least one of a location change, a slope change, a size change and a transformation degree from the first coordinate space to the second coordinate space is expressed as a linear conversion equation. Generally, according to the time when the measurement target 10 is measured and the location where the measurement target 10 exists, the sort and degree of the change is varied. In addition, when the measurement target 10 is changed, the sort and degree of the change is also varied. Thus, conversion coefficients composed of the linear conversion equation are unknown. However, the conversion formula may be set in advance.

Referring again to FIGS. 1 and 2, thereafter, the produced change amount is compensated for to set an inspection area in step S170. Since the change amount of the measurement target 10 is generated by the geometric distortion in measuring the measurement target 10, a wrong inspection area may be corrected when compensating for the change amount.

For example, after the previous processes that the reference data is summoned in step S120 and the measurement data is acquired in step S130, value of the feature variable of the feature object for the reference data and value of the feature variable of the feature object for the measurement data are expressed as the linear conversion equation. Then, the unknown included in the linear conversion equation is acquired to finalize the conversion formula. After the conversion formula is finalized, the inspection area, in which the distortion due to the change amount is compensated for, may be set by using the conversion formula.

According to the inspection method of the present invention, the change amount of the measurement target 10 incurred from the geometric distortion of the measurement target 10 is considered to compensate for the change amount of the measurement target 10. Thus, an inspection area for the measurement target 10 may be correctly set.

Figure 13:
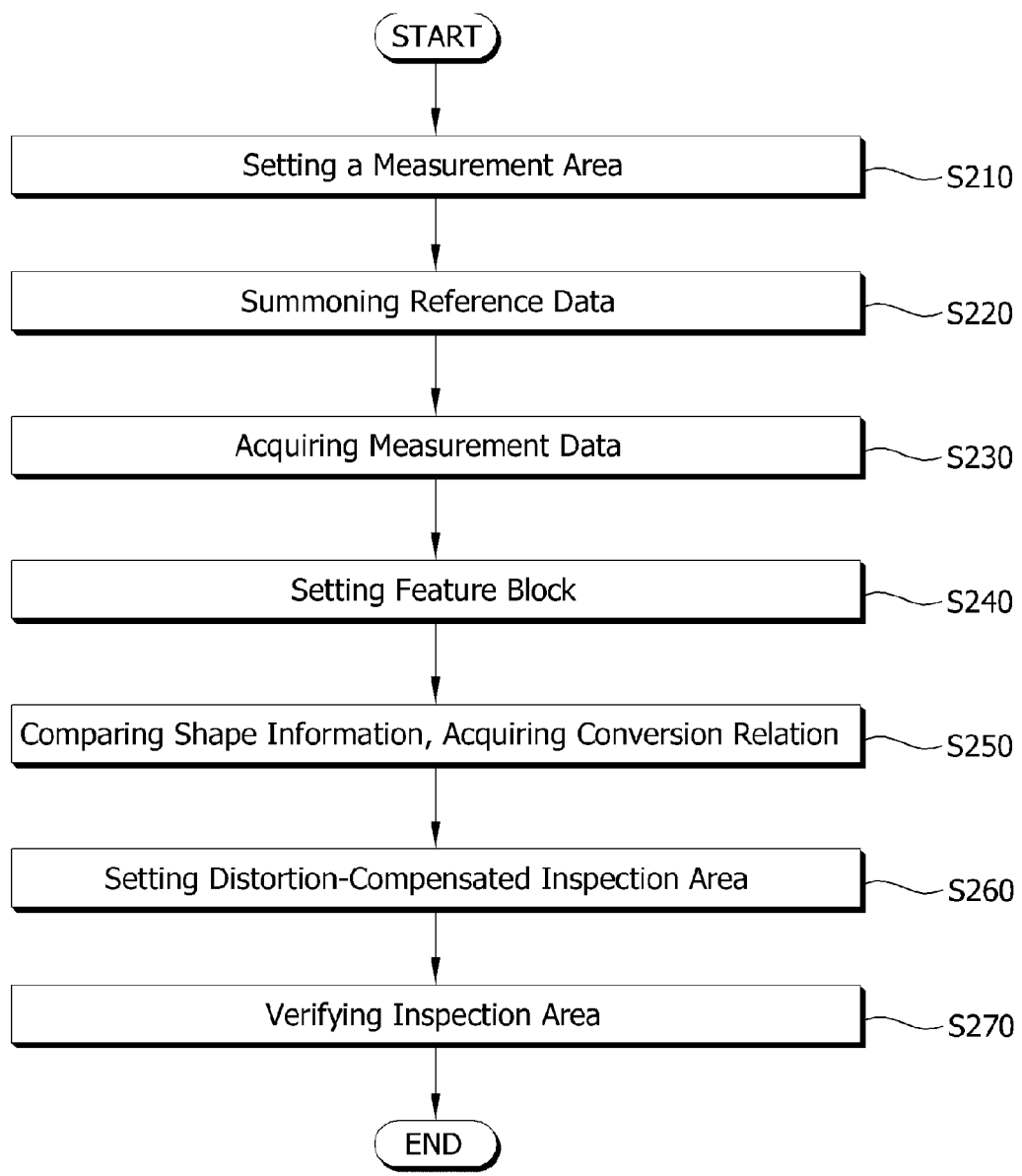
FIG. 13 is a flow chart illustrating an inspection method according to an exemplary embodiment of the present invention.
Figure 14:
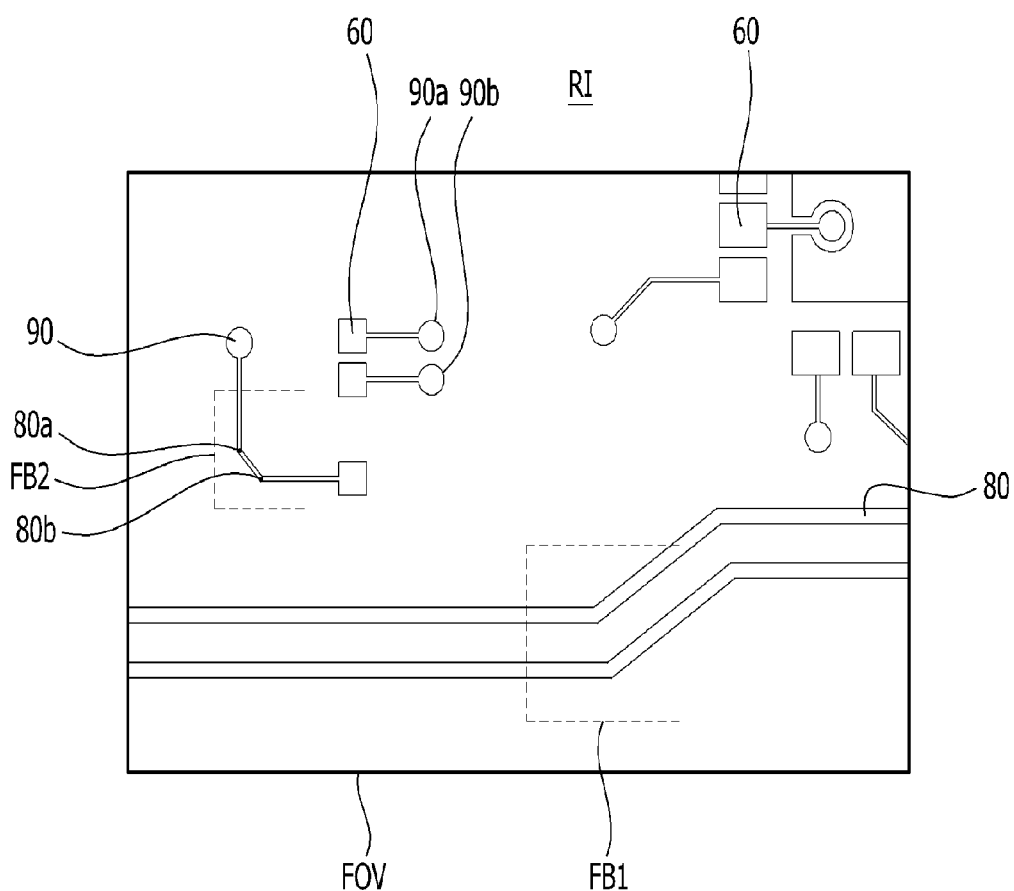
FIG. 14 is a plan view illustrating an example of a reference data in the inspection method illustrated in FIG. 13.
Figure 15:
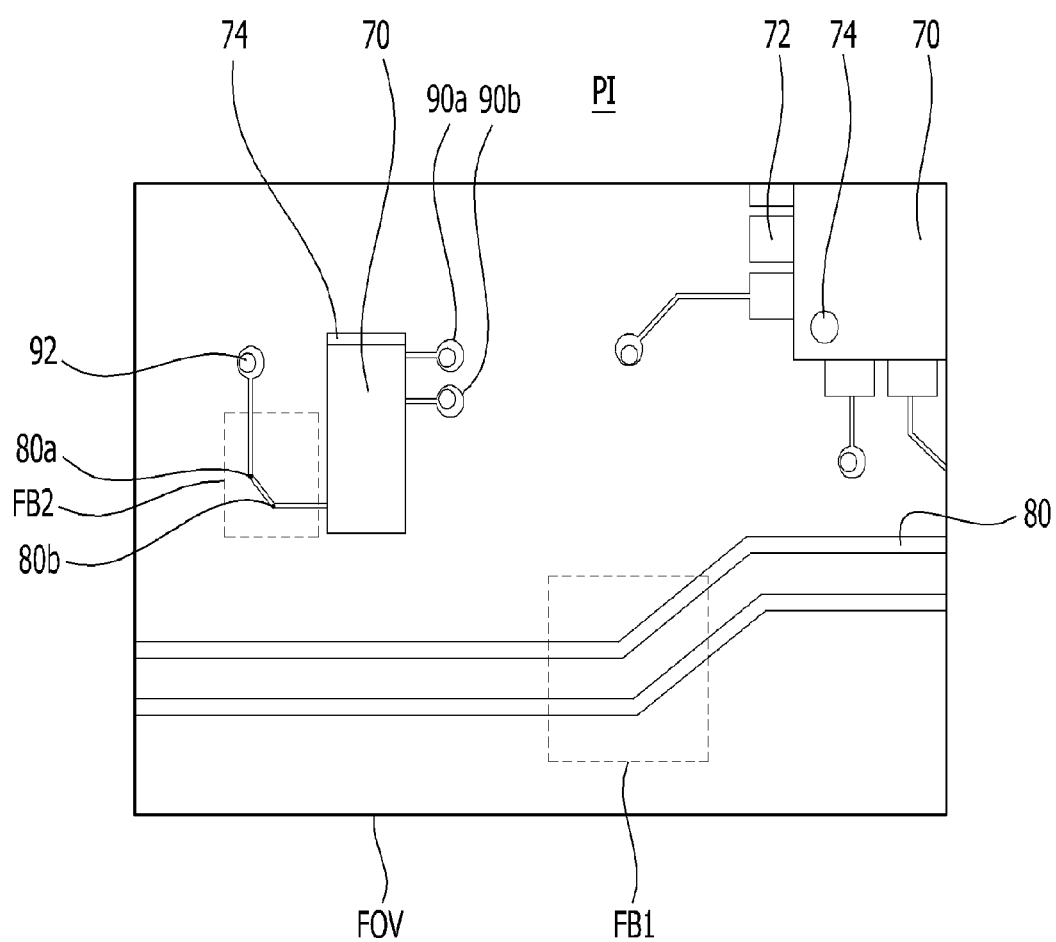
FIG. 15 is a plan view illustrating an example of a measurement data in the inspection method illustrated in FIG. 13.

FIG. 13 is a flow chart illustrating an inspection method according to an exemplary embodiment of the present invention. FIG. 14 is a plan view illustrating an example of a reference data in the inspection method illustrated in FIG. 13. FIG. 15 is a plan view illustrating an example of a measurement data in the inspection method illustrated in FIG. 13.

Referring to FIGS. 13 to 15, in order to set a distortion-compensated inspection area according to an exemplary embodiment of the present invention, first, a measurement area FOV is set on a board in step S210.

The measurement area FOV indicates a predetermined area set on the board so as to inspect whether the board is good or bad, for example. The measurement area FOV may be set based on photographing scope or field of view of the camera 210 employed in an inspection apparatus such as the three-dimensional shape measurement apparatus illustrated in FIG. 1.

Then, a reference data RI for the board including the measurement area FOV is summoned in step S220. The reference data RI may be, for example, as shown in FIG. 14, a theoretical plane image of the board.

In an exemplary embodiment, the reference data RI may be obtained from CAD information or gerber information in which a shape of the board is recorded. The CAD information or the gerber information may include design information of the board, and typically include configuration information of a pad 60, a circuit pattern 80, a hole pattern 90, etc.

In another exemplary embodiment, the reference data RI may be acquired from learning information that is obtained in a learning mode. The learning mode may be realized by processes, for example, such as searching board information in a database, learning a bare board in case that the board information is not in the database, and storing the board information in the database after the board information is produced by learning the bare board. That is, in the learning mode, a bare board of a printed circuit board is learned and design reference information of the printed circuit board is acquired, and the reference data RI may be acquired by obtaining the learning information through the learning mode.

Thereafter, a measurement data PI for the measurement area FOV is acquired in step S230.

The measurement data PI may be, for example, as shown in FIG. 15, a real photographed image for the printed circuit board, in which a part 20 mounted on the board, a terminal 22, a polar indication formed at a part 24, a circuit pattern 80, a hole 92, etc. are shown. The measurement data PI has, as shown in FIG. 15, the same image as the reference data RI except for additional elements such as the part 20. However, the measurement data PI is distorted in comparison with the reference data RI, due to warp, twist, etc. of the board.

In an exemplary embodiment, the measurement data PI may be acquired by illuminating light onto the measurement area FOV using the illumination section of the inspection apparatus, and photographing an image reflected by the illuminated light using a camera installed in the inspection apparatus. Alternatively, the measurement data PI may be acquired by illuminating grating pattern light onto the measurement area FOV using a grating pattern illumination section of the inspection apparatus, photographing an image reflected by the illuminated grating pattern light to obtain data for a three-dimensional shape, and averaging the data for the three-dimensional shape.

Then, at least one feature block is set for a predetermined shape information in the measurement area FOV by a block in step S240.

The predetermined shape information may correspond to the feature object described in FIGS. 1 through 12. The predetermined shape information corresponding to the feature object is set by a block, which may be more correct in comparison with a method of comparing the reference data RI and the measurement data PI based on a coordinate such as a corner point, a circle and a hole.

Since there exists many corner points, circles, etc on the board, in case that corner points 80a and 80b are disposed adjacent or circles 90a and 90b are disposed adjacent as shown in FIGS. 14 and 15, it may be confused when the corner points 80a and 80b and the circles 90a and 90b are compared between the reference data RI and the measurement data PI. For example, it may happen to commit an error that the corner point 80a disposed at an upper portion of the reference data RI may be compared with the corner point 80b disposed at a lower portion of the measurement data PI, or the circle 90b disposed at a lower portion of the reference data RI may be compared with the circle 90a disposed at an upper portion of the measurement data PI. In addition, when a circle 90 and a hole 92 shown in FIGS. 14 and 15 are compared, correct comparison may be not conducted due to precision of hole-drilling, i.e., the hole 92 may be dislocated as shown in FIG. 15.

In contrast, very various shapes exist in the feature block. Thus, according to an exemplary embodiment of the present invention, comparing blocked shape information of the reference data RI with blocked shape information of the measurement data PI may prevent an error in designating a target object for comparison.

When substantially the same shapes repetitively exist in setting the feature block, an error in designating a target object for comparison may happen in comparing shape information within the feature block in the reference data RI with shape information within the feature block in the measurement data PI. Thus, the feature block may be set to remove possibility to mistake the shape information in the feature block for adjacent shape information.

In addition, in order to remove the mistakability, the feature block may be set to have a two-dimensional identifier. Particularly, since the feature block is set at a portion of the reference data RI and a portion of the measurement data PI, as shown in FIGS. 14 and 15, to compare the shape information of the reference data RI with the shape information of the measurement data PI, the feature block may have the two-dimensional identifier capable of defining two-dimensional plane to precisely match the two shape information. For example, a bent line, a quadrangle, a circle and combination thereof may be variously included within the feature block.

One or a plurality of feature blocks may be set in the inspection area, for example, as shown in FIGS. 14 and 15, two feature blocks of first and second feature blocks FB1 and FB2 may be set in the reference data RI and the measurement data PI.

For example, the shape information in the feature block may have a plurality of shapes such as the second feature block FB2, and thus the conversion relation may be correctly acquired. In addition, in this case, at least two shapes of the shapes in the shape information may be substantially the same. That is, even though at least two shapes are substantially the same, the shapes in the shape information are compared by one block to remove mistakability.

In this case, the plurality of shapes in the shape information may have two-dimensional identifier. Thus, mistakability may be reduced in comparing the shape information.

The feature block may be, first, set in the reference data RI, and then the corresponding feature block may be set in the measurement data PI. Alternatively, the feature block may be, first, set in the measurement data PI, and then the corresponding feature block may be set in the reference data RI. In other words, when the feature block is set in one of the measurement data PI and the reference data RI, corresponding feature block may be detected in the other of the measurement data PI and the reference data RI.

Before the feature block is set, the reference data RI and the measurement data PI may be overlaid. After overlaying the reference data RI and the measurement data PI, the feature block may be set to remove mistakability. The overlay may include a concept of physically overlaying an image corresponding to the reference data RI and an image corresponding to the measurement data PI, and a concept of abstractly overlaying the reference data RI and the measurement data PI. After the inspection area is set, which will be described later, the overlay of the reference data RI and the measurement data PI may be also performed to verify the set inspection area.

In an exemplary embodiment, the feature block may be manually set. Particularly, the feature block may be defined by a worker, based on at least one of the reference data RI and the measurement data PI, or the overlaid reference data RI and measurement data PI. For example, the worker may set some blocks that are spaced apart from each other and include a two-dimensional identifier as the feature block in the measurement area FOV. The worker may set a plurality of areas uniformly distributed in the measurement area FOV as the feature block.

Alternatively, the feature block may be automatically set. Particularly, the feature block may be set by image analysis. Areas uniformly distributed in the measurement area FOV may be set as the feature block.

A noise pattern may be removed in the feature block by using the overlay. For example, the measurement data PI may include silk pattern printed on a bare board, which is different from the reference data RI. Thus, in order to correctly compare the shape information, first, a silk pattern is excluded from the measurement data PI or the overlaid reference data RI and measurement data PI. Then, the feature block may be set for the measurement data PI excluding the silk pattern.

Thereafter, the shape information in the reference data corresponding to the feature block and the shape information in the measurement data corresponding to the feature block are compared to acquire conversion relation between the reference data and the measurement data in step S250.

Figure 16:
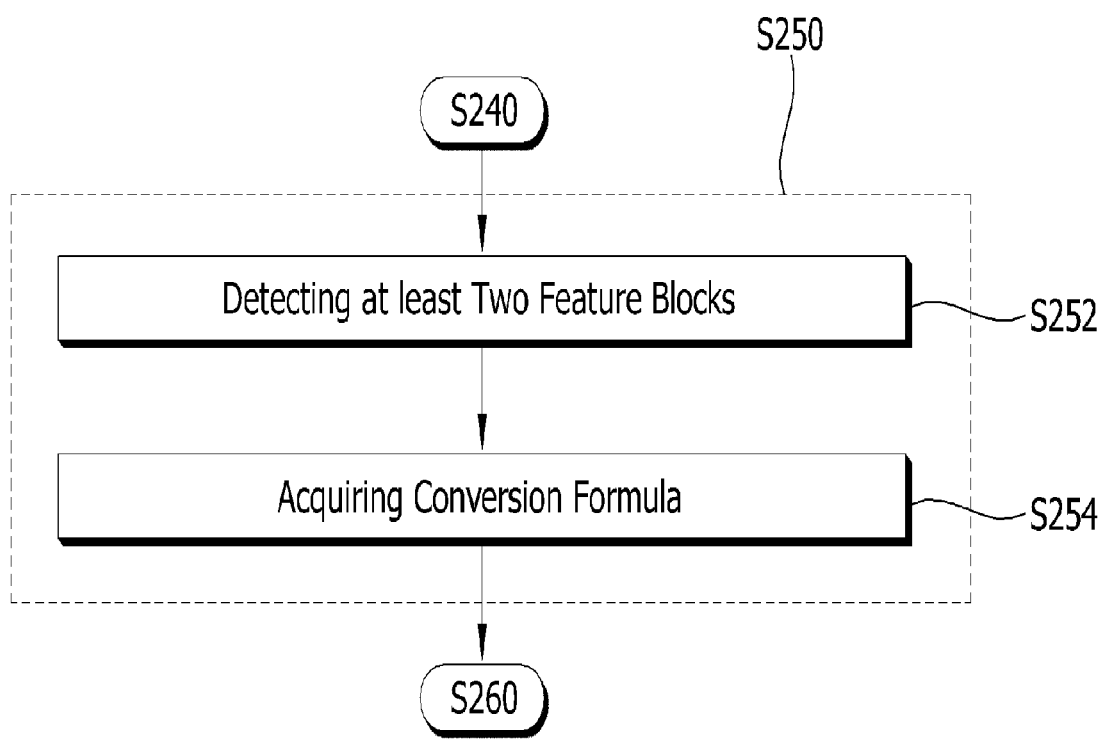
FIG. 16 is a flow chart illustrating an exemplary embodiment of a method of acquiring a conversion relation between the reference data and the measurement data.

FIG. 16 is a flow chart illustrating an exemplary embodiment of a method of acquiring a conversion relation between the reference data and the measurement data.

Referring to FIG. 16, first, at least two feature blocks is selected from a plurality of feature blocks in step S252. For example, the selected feature blocks may be the first and second feature blocks FB1 and FB2 in FIGS. 14 and 15.

Then, a quantified conversion formula between the reference data RI and the measurement data PI is acquired by using the selected at least two feature blocks FB1 and FB2 in step S254. The measurement data PI is distorted due to warp, twist, etc. of the board in comparison with the reference data RI corresponding to theoretical reference information. The conversion formula corresponds to a formula mathematically converting the reference data RI into the measurement data PI to compensate for the distorted degree. The quantified conversion formula may be determined by using at least one of a location change, a slope change, a size, change and a transformation degree, which are acquired by comparing the reference data RI and the measurement data PI corresponding to the selected at least two feature blocks FB1 and FB2.

For example, the conversion formula may be acquired by using Equation 1.

$$P_{CAD}f(tm)=P_{real} \qquad \text{Equation 1}$$

In Equation 1, $P_{CAD}$ is a coordinate of a target in CAD information or gerber information, i.e., a coordinate in the reference data RI, f(tm) corresponds to the conversion formula serving as a conversion matrix or a transfer matrix, and $P_{real}$ is a coordinate of the target in the measurement data PI; which is acquired by a camera. When the theoretical coordinate $P_{CAD}$ in the reference data RI and the real coordinate $P_{real}$ in the measurement data PI are found, the conversion matrix may be known.

For example, the conversion matrix may include a coordinate conversion matrix according to an affine conversion or a perspective conversion, in which point-to-point relation is expressed as a first-order form in an n-dimensional space. In order to define the coordinate conversion matrix, the number of the feature blocks may be properly set, for example, more than or equal to three in case of an affine conversion and more than or equal to four in case of a perspective conversion.

Referring again to FIGS. 13 to 15, then distortion is compensated for by using the conversion relation to set an inspection area for inspecting a measurement target in the measurement area in step S260.

For example, the inspection area for inspecting the measurement target in the measurement area may be set by converting the measurement data PI by using conversion value of distortion degree in the measurement target, which is acquired by the conversion relation, or by applying equation with respect to the conversion relation to the reference data RI for conversion.

Since the conversion relation compensates for the distortion generated in the measurement data PI by comparing the measurement data PI with the reference data RI, the shape in the set inspection area may be nearer to a shape for the real board. The inspection area may be set with respect to the entire area of the measurement area FOV, and may be set with respect to only a predetermined inspection area for which inspection is desired.

For example, after a predetermined inspection area, for which inspection is desired, is set, and an inspection area is set in the measurement data PI by using the conversion relation, various states such as a connection state of parts may be inspected in the inspection area. In the inspection, the measurement data PI may be used, which is previously acquired in a step of acquiring measurement data PI for the measurement area FOV (step S230).

Thereafter, optionally, it may be verified whether the set inspection area is valid or not in step S270.

In an exemplary embodiment, in order for the verification, in addition to a feature block for comparison of the shape information, which is set in a step of setting the feature block (step S240) (hereinafter, refer to as "comparison feature block"), a feature block for verifying validity of the set inspection area (hereinafter, refer to as "verification feature block") may be additionally set. The comparison feature block and the verification feature block may be simultaneously set in a step of setting the feature block (step S240), or the verification feature block may be set later.

Accordingly, it may be judged by using the verification feature block whether the set inspection area of the measurement target is valid or not.

Figure 17:
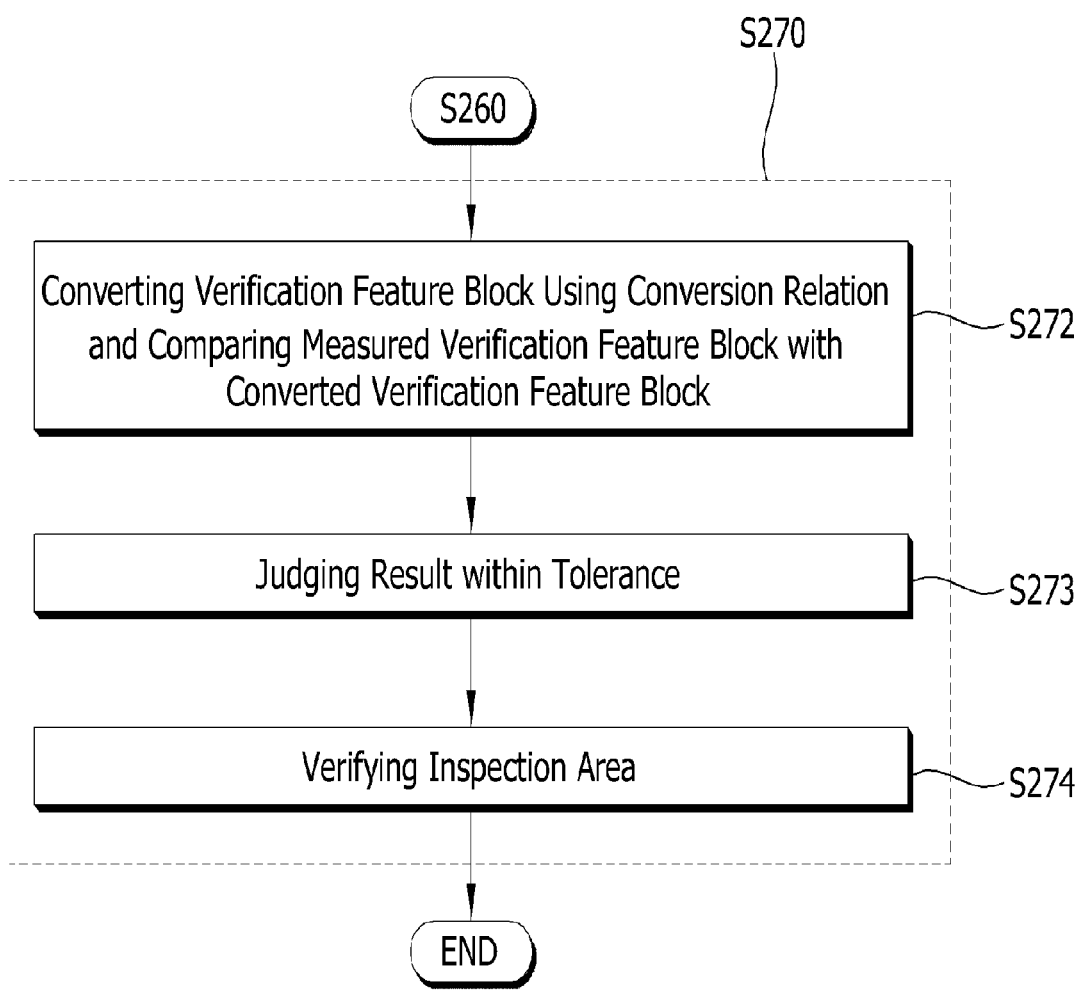
FIG. 17 is a flow chart illustrating an exemplary embodiment of a method of verifying whether the set inspection area is valid.

FIG. 17 is a flow chart illustrating an exemplary embodiment of a method of verifying whether the set inspection area is valid.

Referring to FIG. 17, first, the verification feature block is converted by using the conversion relation, and the converted feature block is compared with actually measured verification feature block in step S272.

Since shape information in the converted verification feature block exists in the set inspection area in which the distortion is compensated for by the conversion relation, in principle, the shape information in the converted verification feature block is locationally almost same as the shape information in the actually measured verification feature block, and it may be judged that the set inspection area is valid.

Then, as a result of the comparison, it is judged whether locational difference is within a tolerance or not in step S273.

For example, after a location, where the shape information in the converted verification feature block is located, is set as a coordinate, and a location, where the shape information in the actually measured verification feature block is located, is also set as a coordinate, it is checked whether difference between the coordinates is within a predetermined tolerance or not. The tolerance may be determined by a size of the board, a board-requiring criterion of judging good or bad, etc.

Then, the set inspection area is verified in step S274.

Particularly, in case that the difference between disposed locations is within the tolerance, the set inspection area is judged valid, and in case that the difference between disposed locations is not within the tolerance, the set inspection area is judged invalid. In case that the set inspection area is judged invalid, the previous processes may be repeated to reset the conversion relation.

According to the above, a predetermined shape information in the measurement area FOV set on the board is set as the feature blocks FB1 and FB2 by a block, and the shape information corresponding to the feature block FB1 and FB2 of the reference data RI and the measurement data PI is compared to acquire the conversion relation between the reference data RI and the measurement data PI, thereby correctly setting the inspection area.

In addition, in case that the shape information corresponding to the feature blocks FB1 and FB2 has a plurality of shapes, the conversion relation may be more correctly acquired. In case that at least two shapes in the shape information are substantially the same, the shapes in the shape information are compared by one block to reduce mistakability.

In addition, when the shape information in the feature blocks FB1 and FB2 has a two-dimensional identifier, mistakability may be reduced in comparing the shape information.

In addition, a work such as an inspection of parts may be performed based on the set inspection area, to thereby more correctly judge whether the board is good or bad.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. An inspection method comprising:
    disposing a measurement target onto a stage;
    summoning a reference data of the measurement target;
    acquiring a measurement data of the measurement target;
    selecting at least one feature object in the measurement data and the reference data of the measurement target;
    extracting at least one feature variable for the selected feature object from each of the reference data and the measurement data;
    producing a change amount of the measurement target by using the feature variable and a quantified conversion formula; and
    compensating for the produced change amount to set an inspection area.

2. The method of claim 1, wherein the measurement target includes a printed circuit board,
    the feature object includes at least one of a pattern, a hole, and a shape of a circuit element and a corner point formed on the printed circuit board, and
    the feature variable includes at least one of a coordinate of a point, a slope of a line, a size of a line and a difference between coordinates of two points.

3. The method of claim 1, wherein the change amount of the measurement target includes at least one of a change amount of vertical slope and a change amount of height.

4. The method of claim 3, wherein the change amount of the vertical slope is acquired using a geometric transformation produced by comparing a plane shape of the feature object selected in the reference data with a plane shape of the feature object corresponding to the selected feature object in the acquired measurement data.

5. The method of claim 1, prior to producing the change amount of the measurement target by using the feature variable and a quantified conversion formula,
    further comprising setting the conversion formula by using at least one of a location change, a slope change, a size change and a transformation degree between the feature variable of the reference data and the feature variable of the measurement data.

6. The method of claim 5, wherein setting the conversion formula comprises:
    setting a coordinate space corresponding to the feature object of the reference data to a first coordinate space;
    setting a coordinate space corresponding to the feature object of the measurement data to a second coordinate space; and
    expressing a coordinate conversion relation equation including at least one of the location change, the slope change, the size change and the transformation degree to convert the first coordinate space to the second coordinate space as a conversion equation including at least one unknown, and
    wherein setting the inspection area comprises:
    expressing the feature variable of the reference data and the feature variable of the measurement data as the conversion equation;
    acquiring the unknown included in the conversion equation to finalize the conversion formula; and
    setting the inspection area in which distortion incurred from the change amount is compensated for by using the finalized conversion formula.

7. An inspection method comprising:
    disposing a measurement target onto a stage;
    summoning a reference data including a first feature object of the measurement target;
    acquiring a measurement data of the measurement target;
    extracting a second feature object corresponding to the first feature object from the measurement data;
    comparing a plane shape of the first feature object with a plane shape of the second feature object to check and quantify a geometric transformation to produce a change amount in a vertical direction of the measurement target; and setting an inspection area based on the change amount.

8. The method of claim 7, wherein the first feature object has a polygon shape.

9. An inspection method comprising:

setting a measurement area on a board;

summoning a reference data for the measurement area;

acquiring a measurement data for the measurement area;

setting at least one feature block in the measurement area by a block;

comparing a first shape information of the feature block in the reference data with a second shape information of the feature block in the measurement data to acquire a conversion relation between the reference data and the measurement data; and compensating for distortion by using the conversion relation to set an inspection area for inspecting a measurement target.

10. The method of claim 9, wherein a plurality of shapes is in the shape information corresponding to the feature block.

11. The method of claim 10, wherein at least two shapes of the shapes in the shape information are substantially the same.

12. The method of claim 10, wherein the shape information has a two-dimensional identifier.

13. The method of claim 10, wherein the feature block is plural, and comparing the shape information corresponding to the feature block in the reference data and the shape information corresponding to the feature block in the measurement data to acquire the conversion relation between the reference data and the measurement data comprises:

selecting at least two feature blocks from the plurality of feature blocks; and acquiring a quantified conversion formula between the reference data and the measurement data by using the selected at least two feature blocks.

14. The method of claim 9, wherein setting at least one feature block for predetermined shape information in the measurement area by a block comprises:

setting a comparison feature block to compare the shape information; and setting a verification feature block to verify validity of the set inspection area of the measurement target, and wherein the method further comprises judging whether the set inspection area of the measurement target is valid or not by using the verification feature block, wherein judging whether the set inspection area of the measurement target is valid comprises:

converting the verification feature block by using the conversion relation;

measuring the verification feature block;

comparing the converted feature block and the measured verification feature block to judge whether location difference between the converted feature block and the measured verification feature block is within a tolerance; and resetting the conversion relation when the location difference is out of the tolerance.

15. The method of claim 9, further comprising overlaying the reference data and the measurement data.

16. The method of claim 15, further comprising removing a noise pattern in the feature block by using the overlay.

* * * * *